US009459206B2

(12) United States Patent
Xu

(10) Patent No.: US 9,459,206 B2
(45) Date of Patent: Oct. 4, 2016

(54) SYSTEM AND APPARATUS FOR MEASUREMENT OF LIGHT SCATTERING FROM A SAMPLE

(71) Applicant: Datacolor, Inc., Lawrenceville, NJ (US)

(72) Inventor: Zhiling Xu, Princeton Junction, NJ (US)

(73) Assignee: DATACOLOR HOLDING AG, Luzern (CH)

( * ) Notice: Subject to any disclaimer, the term of this patent is extended or adjusted under 35 U.S.C. 154(b) by 142 days.

(21) Appl. No.: 13/874,956

(22) Filed: May 1, 2013

(65) Prior Publication Data

US 2013/0293897 A1 Nov. 7, 2013

Related U.S. Application Data

(60) Provisional application No. 61/641,463, filed on May 2, 2012.

(51) Int. Cl.
| | | |
|---|---|---|
| *G01B 11/22* | (2006.01) | |
| *G01N 21/55* | (2014.01) | |
| *G01N 21/00* | (2006.01) | |
| *G08B 21/00* | (2006.01) | |
| *G01C 19/00* | (2013.01) | |
| *G01N 21/47* | (2006.01) | |
| *G01N 21/57* | (2006.01) | |

(52) U.S. Cl.
CPC .......... *G01N 21/4738* (2013.01); *G01N 21/55* (2013.01); *G01N 21/57* (2013.01)

(58) Field of Classification Search
CPC ... G01N 21/4738; G01N 21/57; G01N 21/55
USPC ........ 356/627, 446, 448, 73; 340/540; 702/4
See application file for complete search history.

(56) References Cited

U.S. PATENT DOCUMENTS

| | | | |
|---|---|---|---|
| 4,746,805 A | 5/1988 | Stapleton | |
| 5,155,558 A | 10/1992 | Tannenbaum et al. | |
| 5,394,247 A * | 2/1995 | Vahey et al. | 356/429 |
| 5,400,161 A * | 3/1995 | Lambert, Jr. | 349/1 |
| 5,982,501 A * | 11/1999 | Benz et al. | 356/446 |
| 7,791,740 B2 * | 9/2010 | Finarov et al. | 356/625 |
| 2002/0114494 A1 * | 8/2002 | Komulainen et al. | 382/108 |
| 2004/0135794 A1 * | 7/2004 | Van Aken et al. | 345/600 |
| 2007/0027374 A1 * | 2/2007 | Wihlborg | 600/322 |
| 2008/0285032 A1 * | 11/2008 | Ohkubo | 356/343 |
| 2010/0091269 A1 * | 4/2010 | Lex | 356/73 |
| 2010/0118310 A1 * | 5/2010 | Matsui | G01N 21/8806 356/446 |

OTHER PUBLICATIONS

U.S. Appl. No. 13/327,072, filed Dec. 15, 2011, Zhiling Xu.
Standard Test Methods for Instrumental Measurement of Distinctness-of-Image Gloss of Coating Surfaces, ASTM D5767-95(2004).

* cited by examiner

*Primary Examiner* — Tarifur Chowdhury
*Assistant Examiner* — Sunghee Y Gray
(74) *Attorney, Agent, or Firm* — Leason Ellis LLP

(57) ABSTRACT

An apparatus and method for providing a solution that enables technicians or other technical professionals to obtain accurate gloss, haze and DOI values for a reflecting sample due to the surface conditions of the sample. The apparatus and method allow for the generation of a data model of the surface of a sample using a sensor array designed to detect the divergence of a collimated beam of light reflected off the surface of the sample. The same principle enables technical professionals to obtain accurate haze and clarity values for a transparent or translucent sample that is trans-illuminated by light.

17 Claims, 3 Drawing Sheets

SYSTEM AND APPARATUS FOR MEASUREMENT OF LIGHT SCATTERING FROM A SAMPLE

CLAIM OF PRIORITY

This application claims the benefit under 35 U.S.C. Sec. 119(e) of U.S. Provisional Application No. 61/641,463, filed on May 2, 2012 which is herein incorporated by reference in its entirety.

FIELD OF THE INVENTION

The present invention relates to a system and apparatus for analyzing the appearance features of a sample surface or trans-illuminated sample by an imaging detector which measures the degree of scattering that light undergoes via reflection off the sample surface or via transmission through the sample.

BACKGROUND OF THE INVENTION

Devices for examining the optical properties and surface conditions of samples are known in the art. Generally, measuring devices use a light source which directs light at the surface to be examined and a detector detects this light and evaluates the conditions of the surface based in part on an analysis of the light that interacts with the surface.

The appearance of an object is composed of many elements such as gloss, distinctness of image (DOI), and haze Gloss is an important quality criterion for assessing the quality of paints, coatings, plastic surfaces and the like. Measuring gloss with results that are repeatable and precise is, however, exceptionally difficult. In its general definition, gloss is the property of a surface regarding its ability to reflect light. With high gloss surfaces, the angle of reflection equals the angle of incidence of the incoming light. Thus, the light reflected off the surface is reflected along the same angle as the incoming light, on the opposite side of the perpendicular ray from the surface. However, the more complex the shape, the more difficult it is to accurately measure gloss. Considerable physical deviations within a sample make it difficult to standardize the results of gloss measurements. Thus, due to surface conditions of the sample, the specular angle of the light reflected off the surface can change.

The appearance of an object is comprised of other factors beyond gloss, such as distinctness of image (DOI) and haze When the surface of a sample is not perfectly smooth, the incident light reflected off that surface scatters in a number of different directions from the specular angle. Distinctness of image (DOI) is the measure of this spread in the specular reflection due to scattering by fine surface structures of the sample. Reflection haze refers to a cloudy or milky appearance, also due to scattering of light, and it is defined as the spread of the specular component of the reflected light from a glossy surface.

Gloss meters, such as that described in commonly owned, co-pending application Ser. No. 13/327,072 filed on Dec. 15, 2011, hereby incorporated by reference, are configured to measure and display the results of a technical analysis of the gloss characteristics of a surface.

However, standard gloss meters are not configured to have integrated DOI and haze meters. For example, many of these prior art devices have technical limitations due to component selection and orientation which prevent their modification into DOI meters.

In a typical gloss meter, such as Datacolor's 45G® spectrophotometer, a beam of light is sent onto a sample at a fixed angle (e.g. 60 degrees). A pick-up optical channel is put at the same angle on the opposite side of the sample. Light coming from the sample at the same angle is focused through a pick-up lens and is delivered to a sensor.

However, most gloss meters measure the reflected light at a position of ± several degrees from the specular angle. Therefore, these devices cannot receive and evaluate the amount by which the light spreads from the specular angle due to an irregular surface. The light that is spread 0.3 degrees from the specular is responsible for (DOI). In contrast, the light that is spread farther from the specular angle, for example at 2 degrees from the specular angle, is responsible for narrow-angle haze. The light that is spread farther, for example, at 5 degrees from the specular angle is responsible for wide-angle haze. Thus the prior art devices are limited in their ability to determine true DOI and differentiate that characteristic from the haze characteristic.

The article entitled *Standard Test Methods for Instrumental Measurement of Distinctness-of-Image Gloss of Coating Surfaces*, ASTM D5767-95(2004) hereby incorporated by reference, describes traditional methods of measuring DOI. For example, a device with a narrow aperture for the light source and the detector is used to make measurements at the specular angle and slightly off the specular angle (±0.3 degrees). In an alternative method, light is passed through a narrow slit and is projected onto a specimen, and the reflected image intensity is measured through a sliding comb filter to provide a value of image clarity related to DOI. In a further alternative method, a pattern is projected onto the specimen and the reflected image intensity is measured to provide a value of image clarity. Furthermore, the standard measures and methods to measure reflection haze are known in the art. For example, in one arrangement, the gloss reflectance factor is measured at 30 degrees to the specimen normal, DOI is measured at ±0.3 degrees from the specular direction, and reflection haze is measured at ±0.2 degrees from the specular direction for a narrow-angle, and at ±5 degrees from the specular direction for a wide angle.

Different prior art references have described using these prior art methods to measure DOI. For instance, U.S. Pat. No. 4,746,805, hereby incorporated by reference provides a single meter to measure gloss and DOI of a painted surface. However, this disclosure requires the use of shutters and other mechanical devices that increase the complexity of the meter. What is needed is a DOI meter that has a simplified means of operation and construction.

Likewise, U.S. Pat. No. 5,155,558 to Tannenbaum, herein incorporated by reference, describes a method and apparatus for analyzing the appearance features of a surface using a scanning imaging detector translatable through a sequence focal plane positioned along the optical axis. Tannenbaum describes conventional image analysis using a scanned imagining detector. For example, Tannenbaum describes using Fourier Transformations to convert the scanned pixel intensities into spatial frequency domain datasets. One drawback to this system is that the device is complex in both operation and manufacture. Furthermore, it fails to determine the surface conditions of the sample through analysis of the scatter from the divergence of angles based on focusing the light on the sensor.

As such, what is needed in the art is a mechanism for simplifying and streamlining the generation of DOI, gloss and haze measurements where the light sensor is placed at the focal point of a lens, a collimated beam of light is directed at the lens, and surface characteristics are determined based on the amount of light scattered away from the focal point.

SUMMARY OF THE INVENTION

In accordance with a broad aspect of the present invention, the apparatus and system disclosed herein provide for improved measurement of distinctiveness of image (DOI) and haze of a reflecting sample, and clarity and haze of a transmitting sample, which overcomes the deficiencies inherent in the prior art.

In more particular aspects, in the reflecting-sample embodiment, the present invention provides for a distinctiveness of image measurement device in which a sensor is used to accurately determine the degree of light separation from the specular angle, depending on the distance the light strikes from the center of the sensor. More particularly, a device so-constructed provides a sensor and lens arrangement that allows the system to calculate the gloss, DOI, and reflection haze of a sample. Furthermore, the present device and method provide for multiple measurements of non-uniform surfaces to determine more accurately the surface conditions that are found there. Analogous embodiments for a transmitting sample characterize the transmission haze and clarity of the sample by departure of rays from the direction of the collimated transmitted light.

BRIEF DESCRIPTION OF THE DRAWINGS

The foregoing and other features of the present invention will be more readily apparent from the following details description and drawings of an exemplary embodiment of the invention in which.

DESCRIPTION OF ILLUSTRATIVE CERTAIN EMBODIMENTS OF THE INVENTION

By way of overview and introduction, the present invention concerns a system and apparatus to achieve accurate measurement of the surface characteristics of a sample measured by a spectrophotometer. Specifically, the apparatus and system of the present invention are configured to obtain accurate distinctness of image (DOI) measurements of a given sample.

The apparatus and system provide a solution that enables technicians or other technical professionals to obtain a more accurate DOI value for a given sample. The present invention also allows for a more accurate analysis of the surface structures of a sample by comparing the DOI values of different samples. Those skilled in the art will appreciate that the device and method described herein can be modified to fit a number of design constraints. For example, in a particular embodiment of the described DOI meter, the elements are constructed as a removable module or modules that are separately attached to one another by cables or conduits. These elements are configured to work in combination with a hand-held spectrophotometer such as the Datacolor 45G® spectrophotometer. In the alternative, the DOI meter and system described herein are configured to operate as a separate independent device.

Figure 1:
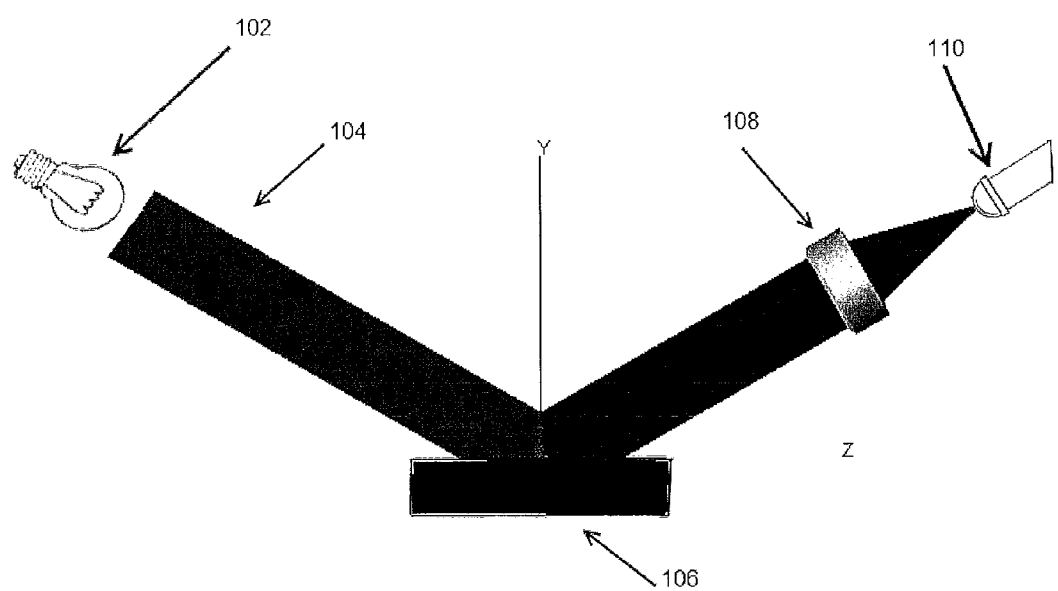
FIG. 1 is an illustrative diagram of the functioning of the device in accordance with an exemplary embodiment of the invention.

As seen in FIG. 1, the illustrated arrangement of components includes a light source 102. The light source 102 projects a beam of collimated illumination 104 onto a sample surface to be measured 106. The light source 102, in one configuration, produces varying intensities of light depending on the specific testing parameters. In the illustrated embodiment, the light source 102 is a single, monochromatic LED lighting element. In alternative arrangements, the light source 102 is a combination of monochromatic LEDs elements. In a further arrangement, the light source 102 is comprised of a plurality of lighting elements, such as tungsten, xenon or fluorescent lighting elements.

All of the light sources incorporated in the illustrated embodiment have variable intensity depending on the testing parameters. In a particular arrangement, the intensity of the light source 102 is altered by a current limiting electrical circuit. In alternative arrangements the illumination is controlled via programmable or non-programmable digital circuitry. In the arrangements of the present invention wherein the device is incorporated into a spectrophotometer, the light source used for color measurement is a suitable light source 102 for the present device. In a further embodiment, the light source contains a plurality of lighting elements; each configured to produce a relatively stable light beam at a given frequency.

The light beam 104 is incident upon a sample 106 to be measured. For example, in one configuration, the light beam 104 is directed at a 60° angle to the surface of the sample 106. In the alternative the light beam 104 is directed at a 30° angle to the surface of the sample 106. In still a further embodiment, the lighting elements are configurable for directing the light beam 104 at a given angle depending on the sample 106 and user input.

In a reflectance arrangement, the light beam 104 is reflected off the surface of the sample 106 such that the reflected light is directed to the lens assembly 108. In the illustrated arrangement of elements, the lens pickup assembly 108 is positioned such that the lens is at the same angle as the incident light beam 104, but opposite to the light source. In another arrangement, the angle and position of the lens assembly 108 are variable so as to enable the lens assembly 108 to match the angle of the incident light beam 104.

The lens assembly 108 is formed of a standard instrument grade lens or lenses. The assembly is designed to be modular for ease of manufacturer and repair. In a particular embodiment, the lens assembly 108 is formed of a plurality of lens elements each designed to focus incoming light at a focal point that is within the structure of the spectrometer. In an alternative arrangement, the lens assembly is designed to place the plurality of lens elements in series so as to provide successive focusing of a light beam on a target of a given size.

In the illustrated arrangement, the lens assembly 108 is configured to focus light reflected off the surface of the sample 106 to a focal point that is within the interior of the apparatus. In an alternative operative mode, there are multiple static lens assemblies and light sources. In this configuration, the proper light source (at the appropriate angle) and the corresponding lens assembly are selected according to user input.

As shown in the illustrated configuration, a sensor array 110 is positioned at the focal point of the lens forming the lens assembly 108. By positioning the sensor array 110 at the focal point, the light beam focused by the lens assembly is directed to the center of the sensor array 110. In the arrangement illustrated in FIG. 1, the sensor array 110 is a photoelectric sensor composed of an array of individual light sensing elements or photosensitive pixels. The sensor array is configured to output a signal that corresponds to the amount of light incident upon the array. The light sensitive elements (not shown) are configured such that each element generates an electrical signal that is representative of the intensity of the light incident upon the particular element. In one arrangement, the sensor array elements are arranged such that there is a single or group of center elements.

Those skilled in the art will appreciate the various designs that are possible for the elements of the sensor array 110. In one arrangement, the sensor array 110 functions by producing an output that is linearly related to the intensity of the received illumination with each element of the array. In an alternative arrangement, the sensor array is configured such that each pixel generates a digital value corresponding to the presence or lack of illumination. In another alternative, each of the elements is configured to provide an independent output depending on the intensity of the light incident upon each element. The sensor array 110 is equipped with sufficient circuitry to allow for the output of each individual element to be known or interpreted by a data logging or processing system. Furthermore, when the sensor elements are saturated, such that the received illumination surpasses a given measurement threshold, and the input-output relationship is no longer linear, the sensor array 110 is configured to output a maximum value corresponding to the acceptable value indicating maximum illumination. In this situation, the sensor array 110 output no longer tracks changes in the input without further correction.

However, even at saturation, the sensor array 110 will continue to respond to an input signal. Thus, measurements obtained above the saturation threshold will not have true values. However, the values relative to each of the elements will still be output from the sensor array 110 to a processor or computer configured to receive the data or signals output from the sensor array.

Figure 2A:
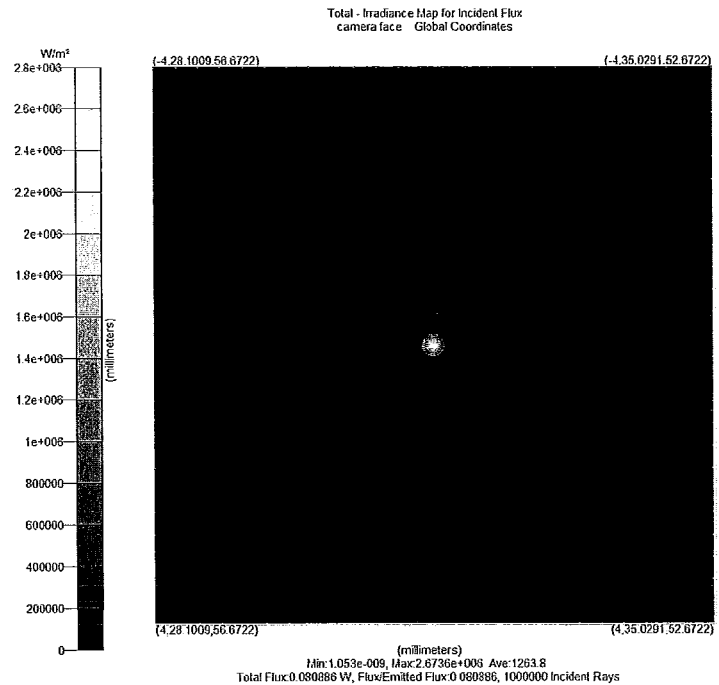
FIG. 2A is an illustrated output of the device according to FIG. 1.
Figure 2B:
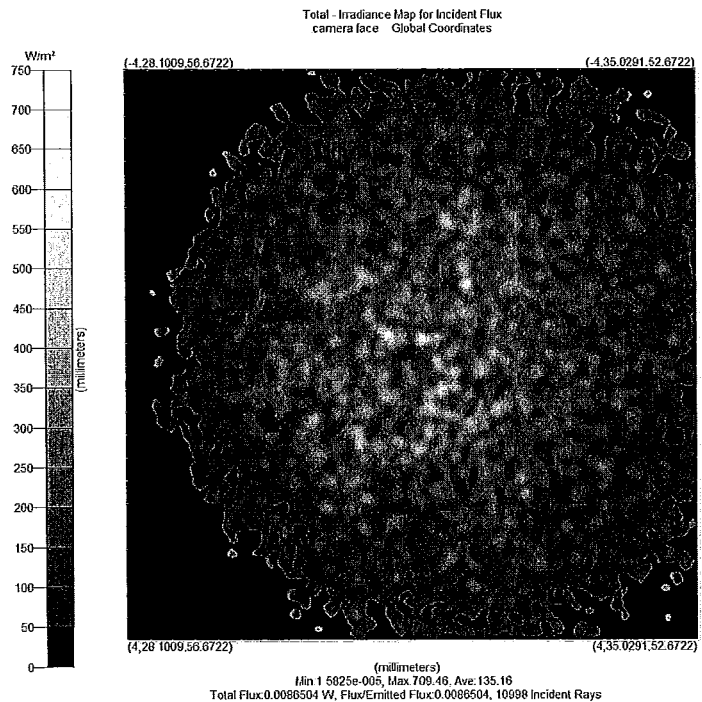
FIG. 2B is an illustrated output of the device according to FIG. 1.

As seen in FIG. 2A-2B, the value of DOI, haze and gloss change depending on the surface characteristics of the sample 106. FIG. 2A depicts the output from the sensory array 110 when the sample 106 is an item of black glass. Due to the uniformity of the surface conditions and the high degree of reflectivity, only a small number of elements within the sensor array are activated. For example, only the center elements of the array receive the light beam 104. This is a result of the collimated beam 104 retaining its uniformity of direction after reflection on a uniform surface. As such, the beam, when focused by the lens assembly, provides only a small amount of light at angles that differ from the specular angle of the beam. The resulting small diameter beam is localized to the center of the sensor array 110. Thus, the degree of reflection haze DOI and gloss can be calculated as a function of the number of sensor elements that receive light beyond the center elements and the intensity of the light received by the sensor.

Conversely, FIG. 2B depicts a sample 106 that is formed of a white colored diffusing material. In this example, the light is scattered more after reflecting off of the diffusing material. As such, the lens assembly fails to focus the light into the center element(s) of the sensor array 110. Instead, the light incident upon the sensor array is in the form of a circular disk of light and not a point. Thus, the spread of light from the specular angle is greater for the irregular surface than for the more regular surface. The number of sensor elements that receive light can be used to determine information about the surface conditions of the sample 106. As the surface structure becomes more irregular, the radius of the circle of light incident upon the sensor gets larger. The apparatus described uses a processor or computer to run an analysis on the relative size of the radius of the circle of light incident upon the sensor array 110 in order to determine information about the surface structure of the sample 106.

In an alternative transmission arrangement, the sample 106 under analysis is a transparent or translucent article. In this arrangement, the collimated light 104 is transmitted perpendicularly through a translucent or transparent sample. The arrangement of elements is such that the light source 102 and lens assembly 108 are arranged such that the light directed through the sample is collected by the lens assembly which is orientated on the opposite side of the sample 106 as the light source 102. As in the above described arrangement, the lens assembly 108 focuses the portion of the light that remains collimated on the focal point of the lens in the lens assembly 108. The sensor 110, as in the reflective embodiment, determines the portion of light that is scattered away from the collimated direct-path. The sensor is configured to measure clarity, haze and transparency based on the amount of light proportionally distant from the center of the sensor array. A narrow pattern indicates a high transparency; broader patterns show increasing haze.

In both arrangements of elements, transmission or reflective, the amount of light falling detected outside the center portion of the sensor can be used to determine the level of haze of the material. In one analysis, the haze characteristic of the sample is related to amount of light received by the sensor at a given distance from the center of the sensor.

Figure 3:
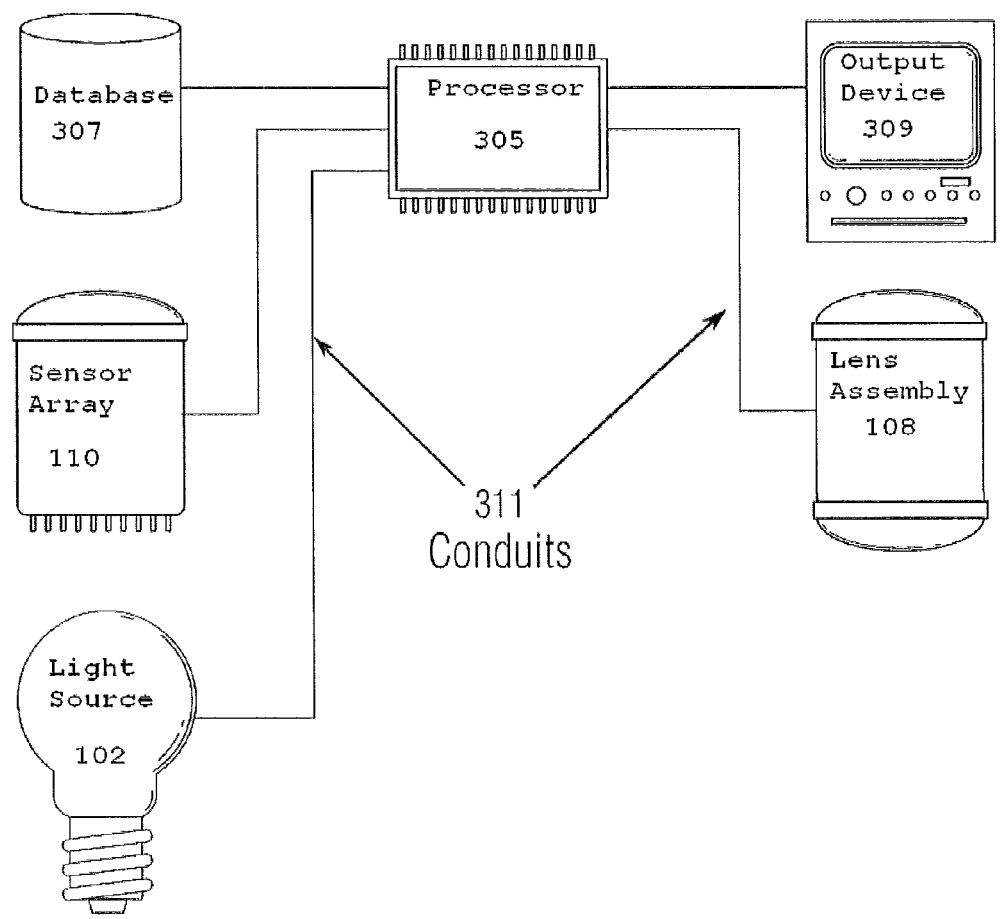
FIG. 3 is a schematic diagram detailing various components of the embodiment FIG. 1.

As seen in FIG. 3, the processor 305 is configured to determine the activation state of each of the elements or pixels of the sensor array 110 and generate a data model having a relation to the physical surface appearance of the sample 106. The computer or processor 305 is connected to the sensor array through communication conduits 311. These conduits permit the bi-directional transmission of information and control data between the sensor array 110 and the processor 305. The data generated by the sensor array 110 is transmitted by the conduits to the processor 305 in order to determine the gloss and off-specular-angle scattering values using widely understood algorithms. The processor 305, through the conduits 311, allows for the control of discrete elements. For example, in a configuration wherein the intensity of the light is variable, the processor 305 is configured to alter the intensity of the light source 102.

Furthermore, the processor is configured to control the lens assembly 108 when necessary to switch between different combinations of lenses and light sources 102. Additionally, the processor 305 is configured to connect to an output device 309 for the display of values or visual alerts depending on the analysis of the data from the sensor array 110. Furthermore, the processor is connected to a storage device or database 307, configured to store data structures or values. In a given arrangement, the processor 305 and the associated linkages 311 are part of the spectrophotometer or larger gloss meter device into which the described arrangement of elements is integrated.

The processor 305 is configured to interpret the data generated from the sensor array 110 and use it to generate data models regarding the surface conditions of the sample 106. For instance, the computer 305 is equipped to perform and analyze the gloss and the DOI values of samples. The computer 305 is equipped to perform statistical analysis on the number of activated pixels to determine the degree DOI or haze given the amount of dispersion that the collimated beam undergoes. For example, statistical analysis and other analytic techniques (such as those described in U.S. Pat. No. 4,746,805); least square fit optimizations, and/or similar computational analysis on the data channels of the sensor analysis are preformed. The computer 305 can be any microprocessor configured to accept the data generated by the sensor array. Those skilled in the art will appreciate the various computational mechanisms available to computer 305 for obtaining data values from the data channel outputs of the sensor array 110.

The processor is equipped with an instruction set that determines the DOI, haze and gloss values depending on the amount and intensity of the light falling upon the pixel elements. In a specific operation of the illustrated device, the processor 305 is pre-configured with set relationship algorithms that govern functions of the sensor array and the light source. In this arrangement, a user inputs a sample type (e.g. diffuse or dark color), and the present device automatically selects and adjusts the proper angle and orientation of the lens assembly and light source. Furthermore, the present device is configured to calibrate the intensity of the light received by the sensor array depending on the intensity of the light source. In this way, a low intensity light source will not provide a false data value regarding the surface conditions of a sample. Additionally, the processor is further configured to compare the data model of a sample to a stored reference data model and alert a user if the data model is below a given threshold.

In operation, the computer 305 generates a data model of the surface conditions of the sample 106 based on the data obtained from the sensor array. The intensity of the light falling on a given pixel, combined with the overall number of pixels activated within a given radius, allows for the creation of a model based on the observed reflected light. The described arrangement of elements, when combined with suitable computer instructions is configured to provide a data model of the surface conditions of a sample. In this embodiment, a collimated light beam 104 is reflected off the surface of the sample 106. This reflected light beam 104 is aimed such that upon reflection, it will strike a lens assembly 108 and will be focused on a sensor array 110. As a result, the processor or computer will generate a data model corresponding to the surface conditions of the sample 106. This data model is then presented to a user, through an output device 309 as a visual display or data table.

The present invention also incorporates a method of using the apparatus described to carry out and achieve the function of generating a data model relating to the surface of a sample. Such a method involves, but is not limited to, an illumination step, wherein a collimated light beam is directed to a sample. A focusing step is provided, wherein the light reflected off of the sample is focused by a lens assembly. A measuring step is provided, wherein a sensor array is located at the focal plane of the focused light and measures the received light. A calculation step is provided wherein the sensor array determines the number of pixels or elements of the sensor array that have been struck by the focused light. Then an analysis step is provided wherein a processor receives as input the information for the sensor array and generates a model of the surface of the sample, such as based on the degree of scattering of the light. Next an output step is provided wherein the surface data model is transformed into a visual indication, providing the user with information regarding the surface.

The above processing functions can be operating as a series of programmed steps preformed by a properly configured computer system using one or more modules of computer-executable code. For instance, a set of software modules can be configured to cooperate with one another to configure a processor so that when executed, they provide accurate color measurement information to a display device as described herein. In this regard, there can be a measuring module, a compensation module, a comparison module and an output module.

A focusing module can be configured as a series of discrete sub-modules designed to access and control the light intensity of the light source and to focus the lens assembly, such that the focused light beam strikes the center of the sensor array.

A measuring module can be configured as a series of discrete sub-modules designed to access and control the sensor array and configure the resulting signals generated from the array elements for output to the calculation module or analysis module.

A calculation module can be configured as a series of discrete sub-modules designed to access the data structures generated by the measuring module and correlate that data to the specific topography or topology of the surface of the sample. For example, the calculation module is configured to determine the relative smoothness of a surface based on the radius of cone of light incident upon the sensor array.

An analysis module can be configured as a series of discrete sub-modules designed to compare the data structures generated by the measuring module and provide comparison analysis to stored base line readings. Furthermore, the analysis module is capable of performing statistical analysis functions on the data structures to determine the extent of the variations in the surface structure.

An output module is provided wherein the result of the calculation module and the analysis module are transformed into visual information for use in a display or visual indication.

Each of these modules can comprise hardware, code executing in a processor, or both, that configures a machine, such as the computing system, to implement the functionality described herein. The functionality of these modules can be combined or further separated, as understood by persons of ordinary skill in the art, in analogous implementations of embodiments of the invention.

It should be understood that various combination, alternatives and modifications of the present invention could be devised by those skilled in the art. The present invention is intended to embrace all such alternatives, modifications and variances that fall within the scope of the appended claims.

While the invention has been particularly shown and described with reference to a preferred embodiment thereof, it will be understood by those skilled in the art that various changes in form and details may be made therein without departing from the spirit and scope of the invention.

What is claimed:

1. An apparatus for measuring the surface or volume optical characteristics of a sample comprising:
   a light source, configured to project a collimated light output in a direction of the sample having an optical scattering characteristic to be measured;
   at least one light focusing device positioned to collect light that has interacted with the sample and focus the collected light;
   at least one sensor array having at least one dimension L, configured with a plurality of sensor elements having a defined sensor area for measuring light incident upon it, the sensor array including a center sensor element positioned so that the sensor area of the center sensor element is positioned at a midpoint of L, the sensor array positioned relative to the at least one light focusing device such that when the collimated light is reflected off of an object light having a substantially high uniformity of surface and a substantially high degree of reflectivity and focused by the light focusing device, the resulting focused beam has a diameter that is equal to or less than the sensor area of the center sensor element of the sensor array, wherein each sensor being configured to output a signal corresponding to the amount of light incident upon the sensor area; and a processor configured to receive the signal generated from each element of the sensor array in response to light incident upon the sample and generate and output an optical scattering characteristic value of the sample as a function of the number of sensor elements having light incident upon them.

2. The apparatus of claim 1, wherein the sensor array is comprised of a plurality of digital light sensing elements.

3. The apparatus of claim 1, wherein the sensor array is comprised of a plurality of analog light sensing elements.

4. The apparatus of claim 1, wherein the processor is configured to determine the amount of light falling on a given portion of the sensor array, wherein the light is not falling on the center of the sensor array.

5. The apparatus of claim 4, wherein the processor is further configured to compare the data model of a sample to a stored reference data model and alert a user if the data model is below a given threshold.

6. The apparatus of claim 1, wherein the optical scattering characteristic of the sample to be measured is a surface scattering characteristic and the light from the light source is reflected off the surface of the sample prior to collection by the at least one light focusing device.

7. The apparatus of claim 6, wherein the processor is further configured to output a visual indication related to the relative smoothness of the surface of the sample.

8. The apparatus of claim 1, wherein the optical scattering characteristic of the sample is a volume scattering characteristic and the light from the light source is transmitted through the sample prior to collection by the at least one light focusing device.

9. The apparatus of claim 8, wherein the processor is further configured to output a visual indication related to the relative transparency of the sample.

10. The apparatus of claim 1, wherein the sensor array is further configured to determine the intensity of the light striking the sensor array.

11. The apparatus of claim 1, wherein the processor is further configured to compare the intensity of the light generated by the light source to the intensity of the light striking the sensor array.

12. A computer-implemented method for utilizing a particular connection with an electronic device in combining a sensor array with a focused collimated light beam to achieve a data model relating to the surface or volume scattering conditions of a sample using a light-geometry-measuring device having a processor, a memory, an input device, an output device and a modeling application stored in the memory and executable by the processor, the method comprising:

projecting a collimated light beam at a specific angle onto or into a sample to be measured;

positioning a lens assembly to collect the light beam after it has interacted with the sample;

focusing the light beam onto a sensor array having at least one dimension L, the sensor array configured with a plurality of sensor elements, each having a defined sensor area for measuring light incident upon it, the sensor being configured to output a signal corresponding to the amount of light incident upon the sensor area, the sensor array including a center sensor element positioned so that the sensor area of the center sensor element is positioned at a midpoint of L; the sensor array positioned relative to the lens assembly; such that when the collimated light is reflected off of an object having a substantially high uniformity of surface and a substantially high degree of reflectivity and focused by the light focusing device, the resulting focused beam has a diameter that is equal to or less than the sensor area of the center sensor element of the sensor array;

receiving with the processor, the signal generated from each element of the sensor array in response to light incident upon the sample;

generating with the processor, an optical scattering characteristic value of the sample as a function of the number of sensor elements that receive light beyond the center element; and creating an output of the optical scattering characteristic value as a visual indication on a display device.

13. The method according to claim 12, wherein the positioning step further comprises:

positioning the lens assembly at the same angle opposite the light beam in order to receive the light beam reflected off the surface of the sample.

14. The method according to claim 12, wherein the positioning step further comprises:

positioning the lens assembly on the opposite side of the sample in order to receive the light beam transmitted through the sample.

15. The method according to claim 12, further comprising the steps of:

dynamically altering the angle or position of the light projected onto the sample; and dynamically altering the angle or position of the lens assembly configured to receive the light that has interacted with the sample so as to intercept the light beam after it has interacted with the sample.

16. The method according to claim 12, further comprising the steps of:

generating a calibration data model from a standardized reference sample;

comparing the sample data model to the calibration data model and determining the optical scattering characteristics of the sample based on the known conditions of the reference sample.

17. The method according to claim 12 further comprising the steps of:

determining the intensity of light striking the entire sensor array; and comparing that intensity to the intensity of the light projected by the light source.

* * * * *